United States Patent [19]

Frignoli

[11] Patent Number: 5,125,899
[45] Date of Patent: Jun. 30, 1992

[54] DISPOSABLE SYRINGE FOR ONCE-ONLY USE

[75] Inventor: Luigi Frignoli, Milan, Italy

[73] Assignee: Abar Service S.R.L., Milan, Italy

[21] Appl. No.: 641,512

[22] Filed: Jan. 15, 1991

[30] Foreign Application Priority Data

Feb. 13, 1990 [IT] Italy .................. 19354 A/90

[51] Int. Cl.$^5$ .................................. A61M 5/00
[52] U.S. Cl. ........................ 604/110; 604/187; 604/218
[58] Field of Search ............ 604/110, 187, 195, 196, 604/191, 240, 241, 242, 243, 218

[56] References Cited

U.S. PATENT DOCUMENTS

| | | | |
|---|---|---|---|
| 2,880,725 | 4/1959 | Kendall | 604/196 |
| 3,667,657 | 6/1972 | Chiquiar-Arias | 222/541 |
| 3,934,586 | 1/1976 | Easton et al. | |
| 3,951,146 | 4/1976 | Chiquiar-Arias | |
| 3,998,224 | 12/1976 | Chiquiar-Arias | |
| 4,233,975 | 11/1980 | Yerman | 604/110 |
| 4,367,738 | 1/1983 | Legendre et al. | |
| 4,710,170 | 12/1987 | Haber | |
| 4,775,364 | 10/1988 | Alles | |
| 4,804,370 | 12/1988 | Haber | |
| 4,813,936 | 3/1989 | Schroeder | 604/195 |
| 4,838,870 | 6/1989 | Haber et al. | 604/187 |

FOREIGN PATENT DOCUMENTS

| | | |
|---|---|---|
| 0229017 | 7/1987 | European Pat. Off. |
| 0282097 | 9/1988 | European Pat. Off. |
| 0326983 | 8/1989 | European Pat. Off. |
| 0360313 | 8/1989 | European Pat. Off. |
| 0340899 | 11/1989 | European Pat. Off. |
| 8810127 | 12/1988 | PCT Int'l Appl. |
| 2015883 | 3/1979 | United Kingdom |
| 2117249 | 10/1983 | United Kingdom |
| 2205750 | 12/1988 | United Kingdom |

*Primary Examiner*—John D. Yasko
*Attorney, Agent, or Firm*—Oblon, Spivak, McClelland, Maier & Neustadt

[57] ABSTRACT

The invention provides a disposable syringe which can be used once only.

The syringe comprises a shaft having a shaped appendix to which a plunger slidable within the syringe cylinder is sealingly connected. At that end at which the hypodermic needle is mounted the cylinder comprises a hole into which a hollow element having a shaped element integral therewith and projecting into the cylinder is inserted and locked. This shaped element becomes securely coupled to a portion shaped complementary to it provided at the adjacent free end of the plunger carried by the shaft to prevent the re-use of the syringe after the shaft has been lowered to firmly engage the shaped portion with the shaped element projecting from the cylinder since withdrawal of the shaft would cause disengagement of the plunger from the shaped appendix of the shaft.

2 Claims, 2 Drawing Sheets

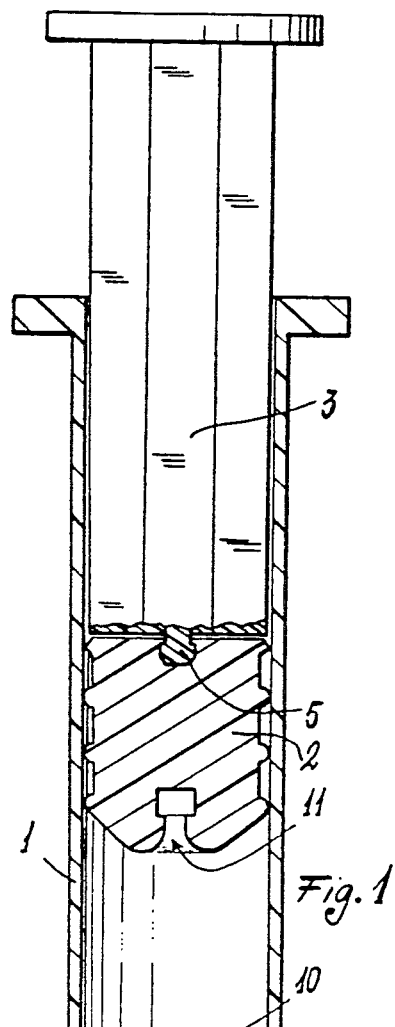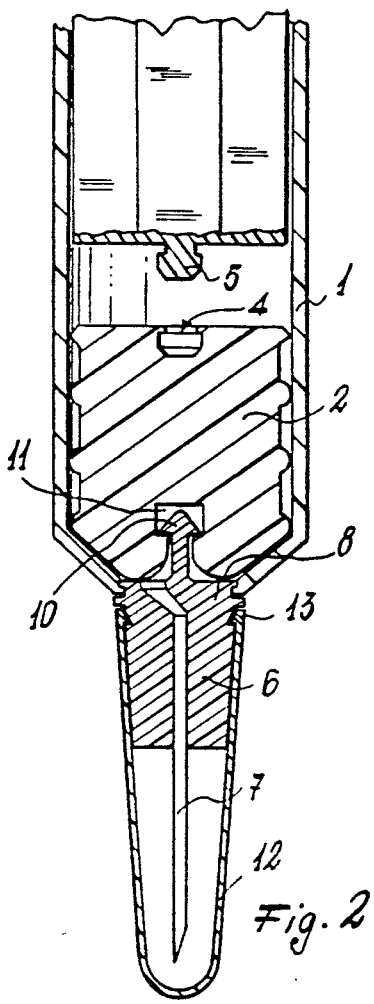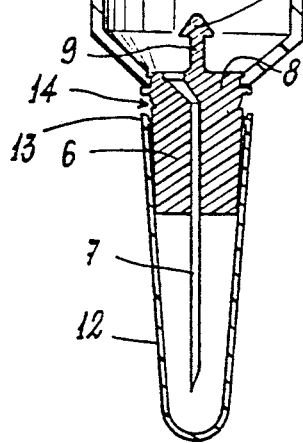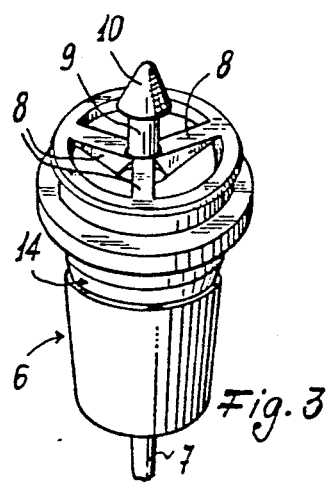

5,125,899

DISPOSABLE SYRINGE FOR ONCE-ONLY USE

BACKGROUND OF THE INVENTION

1. Field of the Invention

This invention relates to a disposable syringe, and more particularly to a syringe which can be used only once, to prevent its re-use particularly by drug addicts.

2. Description of the Related Art

The problem of constructing syringes which can be used only once is very urgent, as is demonstrated by the large member of patents offering different solutions to this problem.

British patent GB-A-2015883 and PCT patent WO 88/10127 describe syringes comprising a plunger fixed only weakly to its shaft and movable within the syringe cylinder, which comprises appendices projecting inwards from the cylinder. These projecting appendices are positioned close to the bottom of the cylinder where the syringe needle is mounted. In this manner, when the plunger is pushed to the bottom of the cylinder the projecting appendices engage the plunger and cause it to separate from the shaft when the shaft is pulled backwards away from the bottom of the cylinder. The drawback of this type of syringe is that it is not possible in practice to make the appendices projecting into the syringe cylinder of sufficient size to ensure reliable engagement of the plunger.

European patent EP-A-00229017 describes a syringe comprising a plunger with a shaped head engaged by a plurality of flexible deformable fingers projecting from the adjacent end of the shaft. When the syringe is used for the first time, on withdrawing the shaft it pulls the plunger back to draw the liquid to be injected into the syringe. Then when the shaft is pushed down the shaped head of the plunger deforms or breaks the flexible fingers engaged with it, after which the fingers can no longer grip the plunger to pull it away from the bottom of the syringe and allow new liquid to be drawn in.

The drawback of this syringe is that its structure is very complicated and of dubious operation because it is unclear how the plunger can be initially pushed to the bottom of the syringe cylinder without breaking the flexible fingers of the shaft, before the syringe is used for the first time to draw in the liquid.

U.S. Pat. Nos. 3,667,657, 3,951,146, and 3,998,224 comprise cutting blades or points which cut or perforate the plunger when this is pressed to the bottom of the cylinder of the respective syringe.

Patent GB-A-2205750 describes a syringe with a plunger transversed by holes below which a flexible membrane is provided to close the holes when pressing the syringe shaft, but which rises from the holes when the shaft is withdrawn from the cylinder, so preventing liquid being drawn into the syringe.

The plunger holes and the relative membrane act as automatic unidirectional valves.

U.S. Pat. Nos. 3,934,586 and 4,367,738 and patent GB-A-2117249 describe syringes in which the cylinders and plungers are shaped with projecting retention teeth and respective seats shaped to allow the shaft to move only in the direction for expelling the liquid, which has to be present in the syringe before it is used, and to prevent the shaft moving in the direction away from the syringe bottom.

SUMMARY OF THE INVENTION

The main object of the present invention is to provide a disposable syringe, i.e. usable only once, which is of simple structure, convenient construction and reliable operation.

These and further objects are attained by a syringe comprising a hollow cylinder with a base wall traversed by a hole at which a hypodermic needle is or can be applied, and a syringe opening shaft movably housed within the cylinder and carrying a plunger releasably connected to a shaped appendix of the shaft, characterised in that in said hole in the cylinder base wall there is inserted and locked a hollow element from which there projects towards the cylinder interior a shaped element securely engageable with a shaped portion complementary to it, provided in the facing surface of the plunger.

BRIEF DESCRIPTION OF THE DRAWINGS

The structure and characteristics of the disposable syringe according to the present invention will be more apparent from the description of some embodiments thereof given hereinafter by way of non-limiting example with reference to the accompanying drawings, in which:

FIGS. 1 and 2 are a schematic axial section through a first embodiment of a syringe, shown before and after use respectively;

FIG. 3 is a perspective view to an enlarged scale of the element fixed to the bottom of the syringe of FIGS. 1 and 2 and provided with a shaped appendix;

FIG. 4 is an axial section through the bottom portion of a different embodiment of the syringe cylinder, with the element provided with the shaped appendix fixed to it;

DESCRIPTION OF THE PREFERRED EMBODIMENTS

Figure 5:
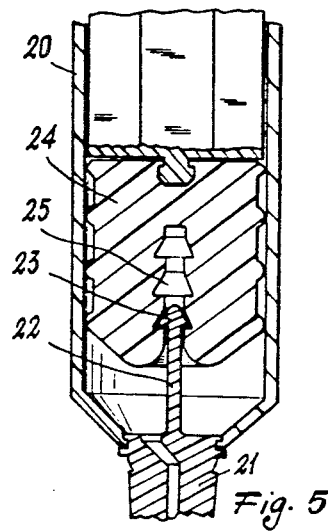
FIGS. 5 and 6 are schematic partial axial sections showing a further embodiment of the syringe.

Reference will firstly be made to FIGS. 1 to 3 which show a syringe comprising a hollow cylinder 1 slidingly housing a seal element represented by a plunger 2 constructed of elastomer material, which is fixed by a weak joint to the lower end of an elongate shaft 3. This weak joint is in the form of a small seat 4 provided in the upper part (with respect to FIGS. 2 and 2) of the plunger, into which there is press-fitted a small shaped appendix 5 projecting from below the shaft (FIG. 1). Under these conditions, when the appendix 5 is housed in the seat 4 of the plunger 2, movement of the shaft relative to the cylinder 1 causes the plunger to move within the cylinder.

In the lower part or base of the cylinder 1 there is provided a passageway into which the upper end (with respect to the figures) of a shaped element 6 is forced from the outside to assume a sealed state, and remains securely fixed to the cylinder either because it snap-fits into it (as shown in the figures) or by friction between two opposing conical surfaces provided in the passageway and on the outer surface of the element 6, or because the element 6 is thermowelded or glued to the cylinder 1. The shaped element 6 is trasversed by a channel which opens at the hypodermic needle 7 (which can either be embedded in the element 6, as shown in the figures, or be pressed over an outer lower conical surface of the element), the upper end of said channel opening into a funnel-shaped recess from which there extend ribs 8 (these being three in number in the case illustrated), from which there projects an elongate appendix 9, the free end of which comprises a widened hook-shaped head 10.

In the plunger 2 there is provided a lowerly (with respect to the figures) open profiled seat 11 into which the head 10 of the appendix 9 can penetrate and remain when the plunger is pushed to the bottom of the syringe by means of the shaft 3.

Initially, before using the syringe, the shaft is in a lowered position with the plunger 2 close to or in light contact with the head 10 of the appendix, but in any event with the head 10 outside the seat 11 in the plunger.

Starting from this initial rest position, after removing the protection cap 12 for the needle 7 (in the illustrated embodiment the cap has sat its open end a hook-shaped projecting edge which is initially in contact with the lower conical surface of the element 6 where it is retained by friction only, as shown in FIG. 1), the plunger is raised from the bottom of the syringe by pulling the shaft 3. It should be noted that during this movement, liquid is drawn into the syringe through the needle 7 without the plunger separating from the shaft because the joint formed by the seat 4 and the appendix 5 inserted into it ensures a sufficiently strong connection to prevent separation of the plunger for the shaft while the liquid is being drawn into the syringe.

When the syringe has been loaded, i.e. filled with liquid, the liquid can be injected in the conventional manner by pressing the plunger with a finger so that the plunger is lowered to the base of the cylinder.

When the plunger 2 comes into contact with the head 10 of the appendix 9, further pressing of the shaft results in insertion of the head 10 into the seat 11 (the plunger deforms elastically, being constructed of a yieldable material) until the head 10 is housed (FIG. 2) in an inner widened part of the seat 11.

In this manner the head 10 is securely held in the seat 11, as is immediately apparent.

At this point, if the shaft is pulled the shaft separates from the plunger because the force with which the head 10 is held in the plunger is greater than the force with which the appendix 5 is held in the plunger. This is easily achieved, for example by simply making the head 10 larger than the appendix 5. This separation of the plunger from the shaft makes the syringe unusable, and it can therefore be used only once.

After making the injection, the cap 12 is placed over the needle 7 and forced down so that its projecting edge 13 snaps securely (FIG. 2) into a groove 14 provided in the outer surface of the element 6, so safely protecting the needle.

FIG. 4 shows a simplified embodiment in which the plunger and shaft (these not being shown for simplicity) are of identical structure to those of FIGS. 1 and 2 or FIGS. 5 and 6, whereas the shaped element to engage the plunger consists of a needle 15 fixed or welded into an aperture provided in the base of the cylinder 16 of a syringe, the upper end 17 of the needle projecting into the cylinder and having at its upper free end a widened head 18 (identical to the aforedescribed head 10) intended to penetrate and fix into the corresponding seat of the syringe plunger.

The cavity in the needle can extend through the entire head 18 of the needle 15, in which one or more holes can also be provided in the immediate vicinity of the base of the cylinder 16. The liquid pushed by the plunger can thus pass through the holes 19 (if provided) or through the cavity in the head 18, or through both if the holes 19 and the cavity in the head 18 are both provided.

In the embodiment described with reference to FIG. 4 it can be seen that the needle 15 has the same purpose as the element 6 from which the appendix projects, its hook-shaped portion being in this case the head 16 of the needle itself.

Figure 6:
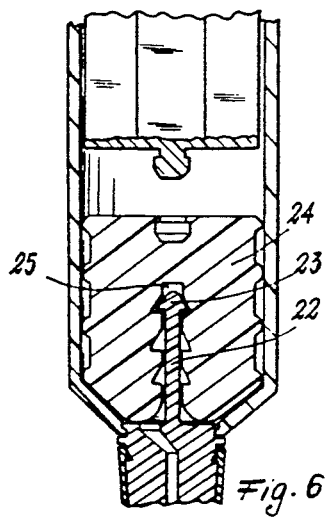

With reference to FIGS. 5 and 6, these represent an embodiment similar to that of FIGS. 1 to 3. They show, fixed to the cylinder 20, a shaped element 21 (of which for simplicity only the upper part is shown) from which there extends an appendix (much longer than the already described appendix 9) with a widened head 23 of hook shape, similar to the head 10.

The seal element, represented by a plunger 24, lowerly comprises a long seat 25 shaped in the manner of successive steps, as can be clearly seen in the drawing.

In contrast to the embodiment shown in FIGS. 1 and 2 in which the plunger 2 is securely hooked by the head 10 of the appendix 9 only when the plunger is pushed practically to the bottom of the syringe, in the embodiment of FIGS. 5 and 6 the plunger 24 is hooked by the head 23 while the plunger is still a long way from the bottom of the syringe, as can be clearly seen in FIG. 5. Already at this point, if an attempt is made to pull the plunger upwards, it disengages from the shaft, this being particularly useful if the syringe is used by drug addicts.

In FIG. 5 the plunger 24 is shown still coupled to the shaft, whereas in FIG. 6 the plunger is shown pushed to the bottom of the syringe and with the shaft pulled upwards and disengaged from the plunger.

Figure 7:
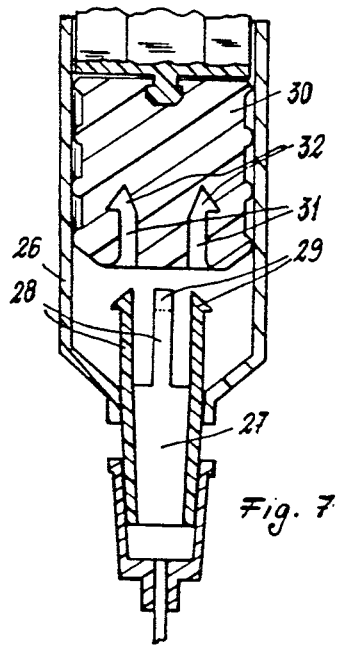
FIGS. 7 and 8 are axial sections through a further embodiment of the syringe, showing the plunger free to slide within the syringe cylinder, and in its locked position on the base of the cylinder respectively.
Figure 8:
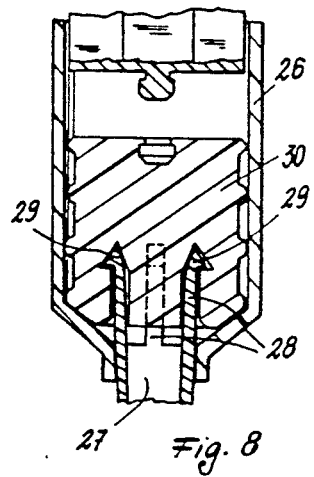

With reference to FIGS. 7 and 8, these show a portion of a syringe in which the cylinder 26 comprises in its base a passageway defined internally by a conical surface into which a shaped element 27 with an at least partly conical surface is forced and securely retained. The element 27 is fixed into said passageway by inserting it from the inside of the cylinder and then pushing it towards the base of the cylinder until the desired secure fit has been obtained.

As can be seen from FIGS. 7 and 8, the element 27 is internally hollow and from that end which lies within the cylinder 26 there project elongate flexible appendices 28 (four in number in the embodiment shown on the drawings) with their free end 29 hook shaped.

In the lower part of the seal element plunger 30 there is provided a profiled annular seat 31 with an enlarged part 32 in its interior.

When the plunger 30 is pushed downwards in the cylinder (from the position of FIG. 7 to the position of FIG. 8) the appendices 28 penetrate into the annular seat 31 in the plunger until the free ends 29 of the appendices penetrate into the enlarged parts 32 of the annular seat, so securely hooking the plunger 30, which disengages from the shaft (FIG. 8) when the shaft is pulled in the direction of withdrawing of the plunger from the base of the cylinder.

Figure 9:
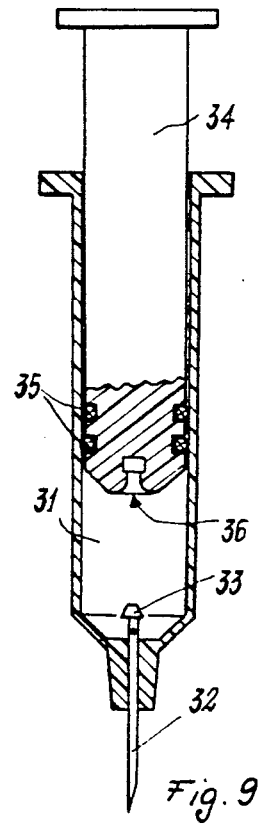
FIGS. 9 and 10, similar to FIGS. 1 and 2, show a syringe in which the shaft is locked on the base of the syringe cylinder after being pushed to the bottom of it.
Figure 10:
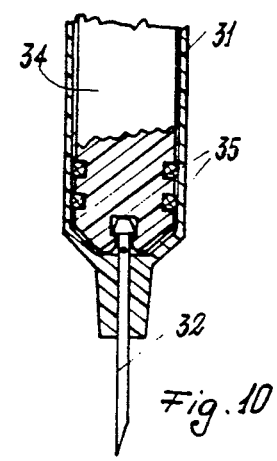

Finally, FIGS. 9 and 10 show a syringe comprising a cylinder 31, in the base wall of which there is mounted a hypodermic needle 32, of which the opposite end to that comprising the needle point projects into the cylinder and has a widened head (similar to that shown in FIG. 4), which forms the shaped fixing element of the syringe.

In proximity to its free end within the cylinder, the syringe operating shaft 34 comprises annular recesses or grooves, each of which houses an annular seal such as an O-ring 35. The free end of the shaft within the cylinder 31 comprises a recess 36 shaped in a manner complementary to the needle head 33. In this manner, when the shaft is pushed to the bottom of the cylinder, the needle head 33 penetrates into the shaped recess 36 provided in the shaft, to become securely fastened within it as shown in FIG. 10.

It can be seen that if the needle 32 is securely fixed to the cylinder 31, the shaft cannot be withdrawn for drawing new liquid into the cylinder after it has been brought into the position (FIG. 10) in which it is fastened onto the needle. If the needle 32 is not fixed securely to the base wall of the cylinder, the needle is withdrawn from the base wall to finish within the cylinder itself if the shaft 34 is pulled with sufficiently high force after fastening onto the needle head 33 (FIG. 10) following the initial operation of the syringe.

Only some possible embodiments of the syringe according to the present invention are shown on the drawings, but it is apparent that the structure of the element carrying the hook-shaped appendices for fastening to the plunger can be easily formed in different but equivalent ways.

In every case it can be seen that the syringe can be used only once, and that it can be produced very easily and at low cost.

I claim:

1. A disposable syringe for once-only use, comprising:
    a hollow cylinder having a base wall traversed by a hole wherein a hypodermic needle is positioned; and
    a syringe operating shaft movably housed within the cylinder and carrying a movable plunger which is releasably connected to a shaped appendix of said shaft;
    wherein said hypodermic needle is inserted and locked in said hole in the cylinder base wall, said hypodermic needle comprising a shaped element which projects from said hypodermic needle towards the cylinder interior, said shaped element being securely engageable with a shaped portion which is provided in a facing surface of said movable plunger, said shaped portion being complementary with said shaped element; and
    an engagement force between the shaped element of said hypodermic needle and the shaped portion in the facing surface of said movable plunger is greater than an engagement force between the shaped appendix of said syringe operating shaft and the movable plunger, such that when said shaft is withdrawn in a direction away from said hypodermic needle, the connection between said shaft and said movable plunger will be released and said movable plunger will remain engaged with said shaped element of said hypodermic needle.

2. A disposable syringe for once-only use, comprising:
    a hollow cylinder having a base wall transversed by a hole wherein a hollow means is positioned; and
    a syringe operating shaft movably housed within the cylinder and carrying a movable plunger which is releasably connected to a shaped appendix of said shaft;
    wherein said hollow means is inserted and locked in said hole in the cylinder base wall, said hollow means comprising a shaped element which projects from said hollow means towards the cylinder interior, said shaped element being securely engageable with a shaped portion which is provided in a facing surface of said movable plunger, said shaped portion being complementary with said shaped element; and
    an engagement force between the shaped element of said hollow means and the shaped portion in the facing surface of said movable plunger is greater than an engagement force between the shaped appendix of said syringe operating shaft and the movable plunger, such that when said shaft is withdrawn in a direction away from said hollow means, the connection between said shaft and said movable plunger will be released and said movable plunger will remain engaged with said shaped element of said hollow means.

* * * * *